United States Patent
Mauduit et al.

(10) Patent No.: US 9,688,641 B2
(45) Date of Patent: Jun. 27, 2017

(54) PROCESS FOR PREPARING ASYMMETRICAL IMIDAZOLIUM SALTS

(71) Applicants: Ecole Nationale Superieure de Chimie de Rennes, Rennes (FR); Centre National de la Recherche Scientifique CNRS, Paris (FR)

(72) Inventors: Marc Mauduit, Vitre (FR); Olivier Basle, Rennes (FR); Mathieu Rouen, Muids (FR)

(73) Assignees: Ecole Nationale Superieure De Chimie De Rennes, Rennes (FR); Centre National De La Recherche Scientifique CNRS, Paris (FR)

( * ) Notice: Subject to any disclaimer, the term of this patent is extended or adjusted under 35 U.S.C. 154(b) by 27 days.

(21) Appl. No.: 14/651,239

(22) PCT Filed: Dec. 11, 2013

(86) PCT No.: PCT/FR2013/053036
§ 371 (c)(1),
(2) Date: Jul. 1, 2015

(87) PCT Pub. No.: WO2014/091156
PCT Pub. Date: Jun. 19, 2014

(65) Prior Publication Data
US 2015/0329494 A1 Nov. 19, 2015

(30) Foreign Application Priority Data
Dec. 12, 2012 (FR) ..................... 12 61969

(51) Int. Cl.
C07D 233/56 (2006.01)
C07D 233/58 (2006.01)
C07D 233/60 (2006.01)

(52) U.S. Cl.
CPC ......... C07D 233/56 (2013.01); C07D 233/58 (2013.01); C07D 233/60 (2013.01)

(58) Field of Classification Search
CPC ... C07D 233/56; C07D 233/58; C07D 233/60
See application file for complete search history.

(56) References Cited

FOREIGN PATENT DOCUMENTS

WO  WO 02094883 A2   11/2002
WO  WO 2009074535 A2  6/2009

OTHER PUBLICATIONS

Meyer et al. "Palladium Complexes with Pyrimidine-Functionalized N-Heterocyclic Carbene Ligands: Synthesis, Structure and Catalytic Activity" Organometallics, 2009, vol. 28, pp. 2142-2149.*
Article—Fernando de Souza et al., "Alternative Synthesis of a Dialkylimidazolium Tetrafluoroborate Ionic Liquid Mixture and its Use in in Poly(acrylonitrile-butadiene) Hydrogenation," *Adv. Synth, Catal.*, vol. 344, No. 2, 2002, pp. 153-155.
Article—Fürstner et al., "Convenient, scalable and flexible method for the preparation of imidazolium salts with previously inaccessible substitution patterns," *Chem. Commun.*, 2006, pp. 2176-2178.
Article—Meyer et al., "Palladium Complexes with Pyrimidine-Functionalized N-Heterocyclic Carbene Ligands: Synthesis, Structure and Catalytic Activity," *Organometallics,*, vol. 28, 2009, pp. 2142-2149.
Article—Ren et al., "A new class of *o*-hydroxyaryl-substituted *N*-heterocyclic carbine ligands and their complexes with palladium," *Journal of Organometallic Chemistry*, vol. 692, 2007, pp. 2092-2098.
International Search Report for PCT/FR2013/053936 dated Feb. 27, 2014, 3 pages.

* cited by examiner

*Primary Examiner* — Joseph Kosack
(74) *Attorney, Agent, or Firm* — Dority & Manning, P.A.

(57) ABSTRACT

The invention relates to a process for preparing an asymmetrical imidazolium salt of formula (1A), in which R1 is an aromatic group, R2 is chosen from a cyclic secondary aliphatic alkyl group and a heteroalkyl group, R3 and R4 are chosen, independently of one another, from the group consisting of hydrogen, a halide and an alkyl group, and A" is an anion. The process comprises a first substep of forming a reaction mixture by bringing one equivalent of an aniline into contact with one equivalent of a compound bearing an amine group, in the presence of at least four point five equivalents of a Brønsted acid. The process also comprises a second substep of forming a solution comprising one equivalent of a dicarbonyl, one equivalent of formaldehyde, and at least four point five equivalents of the Brønsted acid, and adding thereto the reaction mixture formed in the first substep. The mixture is left to stir for a predetermined time at a predetermined temperature. The intermediate asymmetrical imidazolium salt 1A is then isolated.

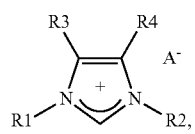

(1A)

13 Claims, No Drawings

PROCESS FOR PREPARING ASYMMETRICAL IMIDAZOLIUM SALTS

CROSS REFERENCE TO RELATED APPLICATION

This application is the national stage entry of International Patent Application No. PCT/FR2013/053036 having a filing date of Dec. 11, 2013, which claims priority to and the benefit of French Patent No. 1261969 filed in the French Intellectual Property Office on Dec. 12, 2012, the entire contents of which are incorporated herein by reference.

The present invention relates to asymmetric imidazolium salts and the method of preparation thereof.

The N-heterocyclic diaminocarbenes (N-heterocyclic carbenes, NHCs) are ligands that are used extensively in organometallic catalysis. This is because the N-heterocyclic diaminocarbene ligands can form highly reactive species when they are associated with a metal. These species are then called diaminocarbene metal complexes.

Among the numerous ligands, we may notably mention the ligands of the imidazolidin-2-ylidene type (saturated NHC), and the ligands of the imidazolin-2-ylidene type (unsaturated NHC). In fact, with a metal, these ligands form complexes that are particularly suitable for organometallic catalysis, The publications *NHCs in Synthesis*, S. P. Nolan, Ed., 2006, Wiley-VCH; *NHCs in Transition Metal Catalysis*, F. Glorius, Ed. 2006, Springer; *N-Heterocyclic Carbenes*, S. D. Diez-Gonzalez, Ed. 2011, RSC Catalysis Series, RSC Publishing, disclose diaminocarbene metal complexes of this type.

It has now been demonstrated that the diaminocarbene metal complexes not only make it possible to increase the yield of certain chemical reactions, but also to perform new chemical reactions that were previously unknown. The diaminocarbene metal complexes have made it possible, for example, to improve the yields of the majority of metal-catalysed reactions, and notably in C—C, C—N, C—O, C—S coupling reactions etc. These coupling reactions are widely used in industrial processes in fine chemistry, as described in the work by Dunetz et al., Chem. Rev. 2011, 111, 2177-2250.

However, it is certainly in the metathesis of olefins that metals bearing N-heterocyclic diaminocarbene ligands have contributed most in terms of improving reaction yields, while allowing significant reductions in the amount of catalyst that is necessary and sufficient for catalysing the reaction. This is notably reported in Grela et al., Chem. Rev. 2009, 109, 3708-3742.

In general, the prior art shows that it is symmetric 1,3-disubstituted diaminocarbene imidazolidin-2-ylidene or imidazolin-2-ylidene ligands that are involved in the organometallic catalytic systems (cf. publications cited above).

Nevertheless, certain disclosures show that 1,3-disubstituted diaminocarbene imidazolidin-2-ylidene or imidazolin-2-ylidene ligands that are asymmetric, and therefore bear non-identical carbon-containing groups, can also be involved in organometallic catalytic systems. Thus, the work of Blechert et al., Dalton Trans. 2012, 41, 8215-8225 shows good reactivities and selectivities for asymmetric carbene ligands. The work by Grubbs et al., J. Am. Chem. Soc. 2011, 113, 7490-7496 shows, moreover, that good reactivities and selectivities can be observed when an N-heterocyclic diaminocarbene ligand bears an aromatic substituent on the one hand and an alkyl group on the other hand.

However, the nature and choice of the carbon-containing groups as substituents are still very limited in regard to the asymmetric 1,3-disubstituted diaminocarbene imidazolin-2-ylidene ligands. This is due in particular to the difficulty of synthesizing the asymmetric imidazolium precursor salts.

In fact, to synthesize an asymmetric 1,3-disubstituted diaminocarbene imidazolin-2-ylidene ligand it is crucial to generate an imidazolium precursor salt first. This synthesis is complex and requires either a very large number of chemical operations (4 to 6 separate chemical operations), or a limited prior choice of carbon-containing substituent groups.

The work by Organ et al., Angew. Chem. Int. Ed., 2007, 46, 2768-2813, and the work by César et al. Chem. Rev. 2011, 111, 2701-2733 show the complexity and the limits of synthesis of asymmetric 1,3-disubstituted diaminocarbene imidazolin-2-ylidene ligands.

The asymmetric 1,3-disubstituted diaminocarbene imidazolin-2-ylidene ligands are of considerable scientific and economic interest, but so far their synthesis is not industrially competitive notably because the number of chemical operations is far too high. Moreover, there is a limited choice of non-identical substituent groups.

The present invention will improve this situation.

Thus, the applicants have developed a method of preparing an intermediate asymmetric imidazolium salt of formula 1A:

(1A)

in which R1 is an aromatic group, R2 is selected from a secondary cyclic aliphatic alkyl group and a heteroalkyl group, R3 and R4 are selected independently of one another from the group consisting of hydrogen, a halide and an alkyl group, and $A^-$ is an anion. The method of the invention is carried out in a single operation and comprises the following steps:

a. forming a reaction mixture by contacting one equivalent (1 eq) of an aniline of formula 2:

(2)

with one equivalent (1 eq) of a compound of formula 3:

(3)

in the presence of at least four point five equivalents (4.5 eq) of a Brønsted acid of formula 4:

AH          (4);

b. forming a solution comprising one equivalent (1 eq) of a dicarbonyl of formula 5:

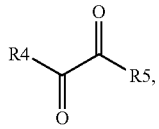

(5)

one equivalent (1 eq) of formaldehyde, and at least four point five equivalents (4.5 eq) of the Brønsted acid of formula 4, heating said solution to about 80° C. and then adding the reaction mixture formed in step a.;
c. stirring for at least 2 hours at about 80'C; and
d. isolating the intermediate asymmetric imidazolium salt of formula 1A.

The method of the invention synthesizes, in just one chemical operation, an intermediate asymmetric imidazolium salt, which notably makes it possible to form 1,3-disubstituted imidazolium salts bearing an aromatic group on the one hand, and a cycloalkyl or heteroalkyl group on the other hand.

Thus, the invention also relates to a method of preparing an asymmetric imidazolium salt of formula 1B:

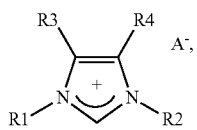

(1B)

in which R1 is an aromatic group, R2 is selected from a secondary cyclic aliphatic alkyl group and a heteroalkyl group, R3 and R4 are selected independently of one another from the group consisting of hydrogen, a halide and an alkyl group, and A⁻ is selected from the group consisting of a tetrafluoroborate anion, a hexafluorophosphate anion, a hexafluoroantimony anion, a tetrakis[(3,5-trifluoromethyl)phenyl]borate anion and a halide anion, said method comprising steps a. to d. mentioned above, and further comprising the steps of:
e. adding one equivalent (1eq) of an inorganic salt and organic solvent, preferably dichloromethane, to the intermediate asymmetric imidazolium salt isolated in step d.;
f. stirring at room temperature for at least one hour and carrying out a water/organic solvent extraction followed by evaporation of said organic solvent;
g. precipitating by a polar organic solvent, then isolating the asymmetric imidazolium salt of formula 1B.

According to one embodiment, the inorganic salt in step e. of the method for preparing the asymmetric imidazolium salt of formula 1B is selected from the group consisting of potassium tetrafluoroborate, sodium tetrafluoroborate, lithium tetrafluoroborate, hydrogen tetrafluoroborate, ammonium tetrafluoroborate, potassium hexafluorophosphate, sodium hexafluorophosphate, lithium hexafluorophosphate, hydrogen hexafluorophosphate, ammonium hexafluorophosphate, silver hexafluoroantimony, potassium hexafluoroantimony, sodium hexafluoroantimony, lithium hexafluoroantimony, potassium tetrakis[(3,5-trifluorom- ethyl)phenyl]borate, sodium tetrakis[(3,5-trifluoromethyl)phenyl]borate and lithium tetrakis[(3,5-trifluoromethyl)phenyl]borate and halogen acid.

The intermediate asymmetric imidazolium salt prepared according to the method of the invention also makes it possible to form zwitterionic 1,3-disubstituted imidazolium salts bearing an aromatic group on the one hand, and a heteroalkyl group on the other hand.

Thus, the invention also relates to a method of preparing an asymmetric imidazolium salt of formula 1C:

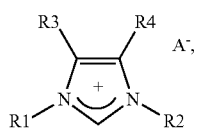

(1C)

in which R1 is an aromatic group, R2 is a heteroalkyl group, R3 and R4 are selected independently of one another from the group consisting of hydrogen, a halide and an alkyl group, and A⁻ is a negative charge on group R2, said method comprising steps a. to d. mentioned above, and further comprising the steps of:
h. adding at least ten equivalents (10 eq) of a carbonate base to the intermediate asymmetric imidazolium salt isolated in step d.;
i. isolating the asymmetric imidazolium salt of formula 1C.

According to one embodiment, the carbonate base in step h. of the method of preparing the asymmetric imidazolium salt of formula 1C is selected from the group consisting of sodium bicarbonate, potassium bicarbonate, sodium hydrogen carbonate and potassium hydrogen carbonate.

In general, in step h. it is necessary to add at least ten equivalents (10 eq) of a carbonate base. More precisely it is necessary to envisage the addition of one additional equivalent compared to the equivalents of Brønsted acid added in steps a. and b.; in other words, if 5 equivalents of Brønsted acid had been added in step a. and 5 equivalents of Brønsted acid in step b. (i.e. 10 equivalents in total), it is necessary to envisage the addition of 11 equivalents of a carbonate base to form the zwitterion.

According to one embodiment, the Brønsted acid of formula 4 in steps a. and b. is acetic acid, This allows a good yield for obtaining the intermediate salt.

Advantageously, in said formulae 1A and 1B, R1 is selected from the group consisting of 2,4,6-trimethylphenyl, 3,5-dinitrophenyl, 2,4,6-tris(trifluoromethyl)phenyl, 2,4,6-trichlorophenyl, and hexafluorophenyl; and R2 is selected from the group consisting of cyclopentyl, cyclohexyl, cyclooctyl, cyclodecyl, cyclododecyl, and cyclopentadecyl. In fact, selection from these groups gives good steric stability.

Advantageously, in said formula 1C, R1 is selected from the group consisting of 2,4,6-trimethylphenyl, 3,5-dinitrophenyl, 2,4,6-tris(trifluoromethyl)phenyl, 2,4,6-trichlorophenyl, and hexafluorophenyl; and R2 is selected from the group consisting of 3-methyl butanoate and 3,3-dimethyl butanoate. R2 can, moreover, be a cyclic heteroalkyl such as a cyclic polyether for example.

According to one embodiment, R3 and R4 are each hydrogen.

The present invention also describes a novel category of asymmetric imidazolium salt. These novel salts can be obtained by the method according to the invention.

Thus, the invention relates to an asymmetric imidazolium salt of formula 1D:

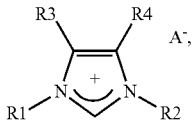

(1D)

in which R1 is an aromatic group, R2 is a secondary cyclic aliphatic alkyl group, R3 and R4 are selected independently of one another from the group consisting of hydrogen, a halide and an alkyl group, and A⁻ is an anion.

Preferably, R1 is selected from the group consisting of 2,4,6-trimethylphenyl, 3,5-dinitrophenyl, 2,4,6-tris(trifluoromethyl)phenyl, 2,4,6-trichlorophenyl, and hexafluorophenyl, and R2 is selected from the group consisting of cyclopentyl, cyclohexyl, cycloheptyl, cyclooctyl, cyclodecyl, cyclododecyl, and cyclopentadecyl. According to one embodiment, R3 and R4 are each hydrogen.

In a preferred embodiment, A⁻ is a tetrafluoroborate anion, a hexafluorophosphate anion, an acetate anion, a hexafluoroantimony anion, a tetrakis[(3,5-trifluoromethyl)phenyl]borate anion or a halide anion. This provides good reactivity and stability.

The present invention reacts an aniline (aromatic amine) and an aliphatic amine (including heteroalkyls bearing an amine function) in particular conditions and in the presence of dicarbonyl, of formaldehyde and of Brønsted acid.

The general synthesis reaction for preparing the intermediate asymmetric imidazolium salt according to the invention is shown below:

General reaction scheme: synthesis of the intermediate asymmetric imidazolium salt according to the invention.

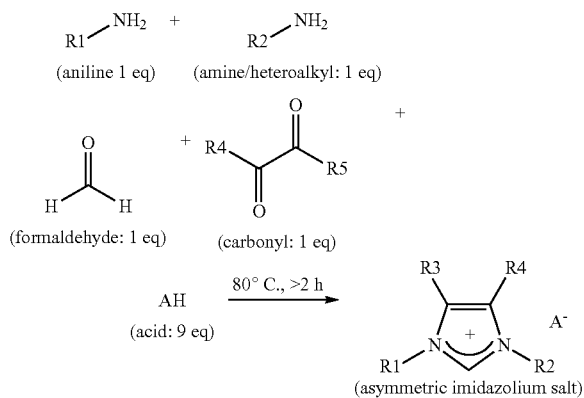

It should be noted that when a heteroalkyl is reacted with the aniline, the formaldehyde and the carbonyl, this heteroalkyl must necessarily contain an amine function. This is notably the case with the alpha-amino acids or the beta-amino alcohols.

The single operation of the chemical synthesis according to the present invention comprises substeps. Thus, in a first substep a reaction mixture is formed by contacting one equivalent (1 eq) of an aniline with one equivalent (1 eq) of an amine (or heteroalkyl) in the presence of at least four point five equivalents (4.5 eq) of a Brønsted acid. Then, in a second substep, a solution is formed comprising one equivalent (1 eq) of a dicarbonyl and one equivalent (1 eq) of formaldehyde in the presence of at least four point five equivalents (4.5 eq) of a Brønsted acid similar to the Brønsted acid in the first substep. This solution is then heated to about 80° C. The mixture formed in the first substep is then added slowly (for example dropwise) to the solution formed in the second substep. The reaction mixture obtained is then stirred for at least 2 hours at about 80° C., before isolating the asymmetric imidazolium salt by extraction/filtration.

The Brønsted acid used for said first and second substeps is preferably acetic acid for reasons of yields. In these conditions, an asymmetric imidazolium salt is obtained composed of an imidazolium cation and an acetate anion. However, other strong acids can be used.

The applicants discovered, surprisingly, that when an aromatic amine and an aliphatic amine are brought into contact in the conditions described above, their difference in reactivity greatly minimizes the formation of the 1,3-bis-aryl and 1,3-bis-alkyl imidazolium salts, which are the reaction by-products resulting from a reaction of auto-condensation of the amines present in the reaction mixture.

Thus, according to the invention, the selectivity can reach a ratio of 1/30/1 in favour of the desired asymmetric imidazolium salt (more precisely: 1 part of the first symmetric salt, 1 part of the second symmetric imidazolium salt, and 30 parts of the asymmetric imidazolium salt). This salt can be called an intermediate asymmetric imidazolium salt in the present description. In fact, the intermediate asymmetric imidazolium salt can be submitted to additional steps in order to proceed to conditioning steps and to transform it partially if necessary.

Following this method of synthesis, by bringing an aniline and an aliphatic amine (including heteroalkyls) into contact, precursor salts of diaminocarbenes of the 1-aryl-3-cycloalkyl-imidazolin-2-ylidene or 1-aryl-3-heteroalkyl-imidazolin-2-ylidene type could be isolated at good yields, permitting exploitation on an industrial scale. Moreover, purification can be carried out by crystallization of the imidazolium salt formed, which further increases the interest in exploitation on an industrial scale.

In a first embodiment, the intermediate asymmetric imidazolium salt obtained by the above method can next be submitted to other substeps in order to exchange the anion resulting from said first and second substeps for another anion promoting reactivity or stability over time. Among these anions, we may notably mention the tetrafluoroborate anion ($BF_4^-$), hexafluorophosphate anion ($PF_6^-$), hexafluoroantimony anion ($SbF_6^-$), tetrakis[(3,5-trifluoromethyl)phenyl]borate anion ($B(C_6F_5)_4^-$), and the halide anions (X⁻, where X is a halogen). This ion exchange is advantageously carried out when the aim is synthesis of compounds of the 1-aryl-3-cycloalkyl-imidazolin-2-ylidene type. Thus, a third substep can consist of adding one equivalent (1 eq) of an inorganic salt and solvent (preferably dichloromethane), to the intermediate asymmetric imidazolium salt isolated (after stirring for at least 2 hours at about 80° C. and the extraction/filtration described above). The mixture obtained is stirred at room temperature until said solvent evaporates. Then the salt can be precipitated with a polar organic solvent, and isolated.

In a second embodiment, the intermediate asymmetric imidazolium salt obtained by the method described above can be submitted to a treatment with a carbonate base. This treatment can lead to the zwitterionic salt being obtained. It should be noted that the salt in the form of a zwitterion is advantageously obtained when investigating the synthesis of compounds of the 1-aryl-3-heteroalkyl-imidazolin-2-ylidene type. Thus, a fourth substep can consist of adding at least ten equivalents (10 eq) of a carbonate base to the intermediate asymmetric imidazolium salt isolated (after stirring for at least 2 hours at about 80° C. and the extraction/filtration described above). The zwitterionic asymmetric imidazolium salt can then be isolated.

The choice of substituent groups is made during formation of the intermediate asymmetric imidazolium salt, namely in the main operation comprising said first and second substeps.

In one embodiment, R1 is preferably selected from the group consisting of 2,4,6-trimethylphenyl, 3,5-dinitrophenyl, 2,4,6-tris(trifluoromethyl)phenyl, 2,4,6-trichlorophenyl, and hexafluorophenyl; and R2 is preferably selected from the group consisting of cyclopentyl, cyclohexyl, cycloheptyl, cyclooctyl, cyclodecyl, cyclododecyl, and cyclopentadecyl. These groups offer good steric stability. R3 and R4 are preferably each hydrogen.

Taking as an example a group R1 of 2,4,6-trimethylphenyl, a group R2 of cyclohexyl and groups R3 and R4 of hydrogen, and following the method described above, a 1-aryl-3-cycloalkyl-imidazolin-2-ylidene of the following formula 6 is obtained:

Reaction scheme: synthesis of intermediate asymmetric imidazolium salt in which R1 is 2,4,6-trimethylphenyl and R2 is cyclohexyl.

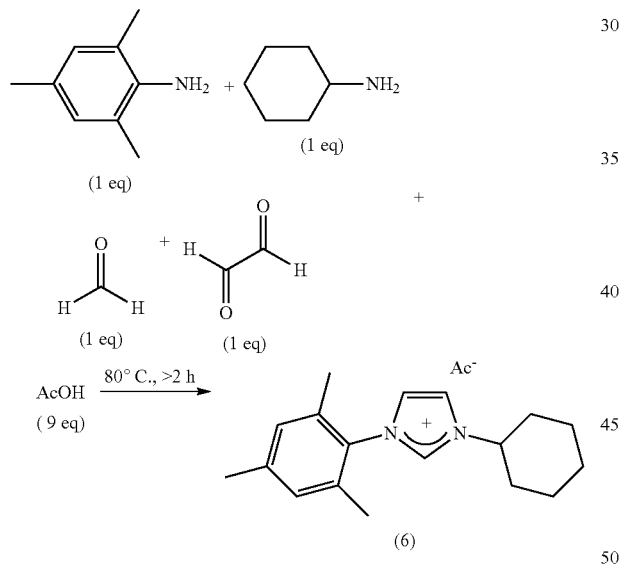

Reaction scheme: synthesis of intermediate asymmetric imidazolium salt in which R1 is 2,4,6-trimethylphenyl and R2 is cyclohexyl.

To determine the selectivity of the reaction, the reaction mixture comprising the 1-aryl-3-cycloalkyl-imidazolin-2-ylidene salt of formula 6 is cooled to room temperature. Then water is added, followed by solvent (for example in ethyl acetate or dichloromethane). The aqueous phase is extracted (for example three times) with the solvent. The organic phases are combined and dried over an anionic salt (for example over magnesium sulphate). Then the organic phase is concentrated under vacuum. Nuclear magnetic resonance (NMR) analysis of the crude reaction product can allow the selectivity of the reaction to be determined.

Exchange of the acetate anion for another anion can be carried out as follows: the crude reaction product is dissolved in solvent (for example dichloromethane). Then 1 equivalent of the inorganic salt comprising the desired counter-anion is added (for example potassium tetrafluoroborate to obtain a tetrafluoroborate counter-anion). The mixture is then stirred at room temperature for some hours (for example 3 h). Then, a liquid/liquid extraction is carried out, namely a water/organic solvent extraction. For this, water is added and the organic phase is separated from the aqueous phase. The aqueous phase is washed (for example three times with solvent. Each organic phase is dried over an anionic salt (for example over magnesium sulphate), and concentrated under vacuum. Generally a brown oil is obtained, to which an organic solvent is added for precipitation (for example ethyl acetate). Then the mixture can be submitted to ultrasonic treatment for some minutes (for example 5 minutes). A solid forms, which is filtered on a frit, then washed with solvent (for example with ethyl acetate) to give the desired asymmetric imidazolium with a desired anion (for example a tetrafluoroborate anion).

In general, the aforementioned precipitation with a polar organic solvent can be performed using ethyl acetate, diethyl ether, or crystallization in ethanol. Precipitation with ethyl acetaté is preferably used.

With the above operating procedure, which only comprises a single chemical operation, the applicants were able to synthesize a large number of novel molecules. Notably, the applicants synthesized the asymmetric imidazolium salts of formulae 7, 8, 9, 10, 11, 12, 13, 14 and 15:

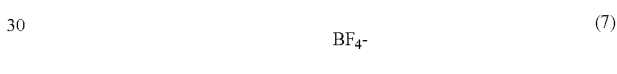

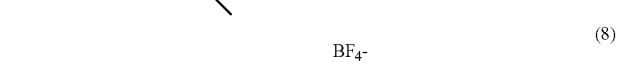

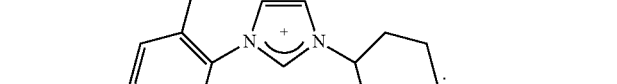

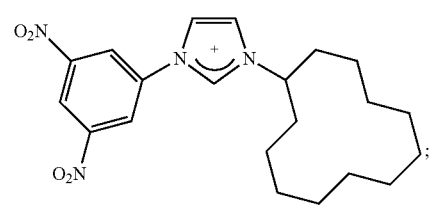

-continued

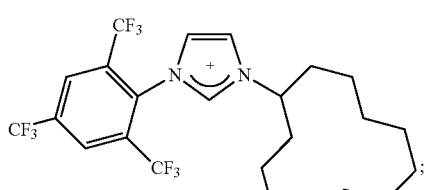
(11)

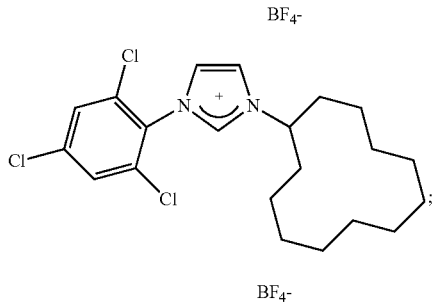
(12)

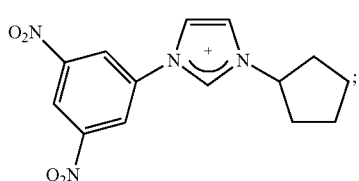
(13)

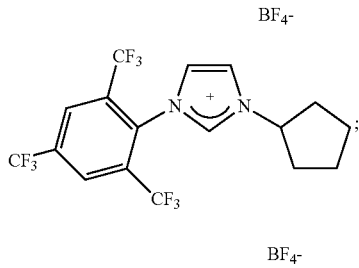
(14)

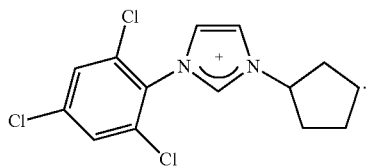
(15)

In general, the applicants synthesized asymmetric imidazolium salts of formula 1D

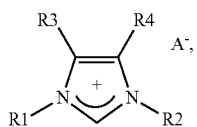
(1D)

in which R1 is an aromatic group, R2 is a secondary cyclic aliphatic alkyl group, R3 and R4 are selected independently of one another from the group consisting of hydrogen, a halide and an alkyl group, and A⁻ is an anion.

R1 can notably be 2,4,6-trimethylphenyl, 3,5-dinitrophenyl, 2,4,6-tris(trifluoromethyl)phenyl, 2,4,6-trichlorophenyl, or hexafluorophenyl.

R2 can notably be cyclopentyl, cyclohexyl, cycloheptyl, cyclooctyl, cyclodecyl, cyclododecyl, or cyclopentadecyl.

R3 and R4 can each be hydrogen. R3 and 4 can also be halides (for example a chlorine atom or alkyl halides). R3 and R4 can also be alkyl groups (for example methyl, ethyl, propyl or isopropyl).

The anion A⁻ can notably be a tetrafluoroborate anion, a hexafluorophosphate anion, an acetate anion, a hexafluoroantimony anion, a tetrakis[(3,5-trifluoromethyl)phenyl]borate anion and a halide anion.

Moreover, taking as an example a group R1 of 2,4,6-trimethylphenyl, a group R2 of heteroalkyl (the compound of formula 3 being valine) and groups R3 and R4 of hydrogen, and following the method described above, a 1-aryl-3-heteroalkyl-imidazolin-2-ylidene of the following formula 16 is obtained:

Reaction scheme: synthesis of the intermediate asymmetric imidazolium salt in which R1 is 2,4,6-trimethylphenyl and R2 is a heteroalkyl.

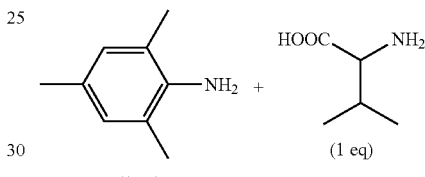

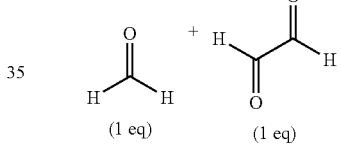

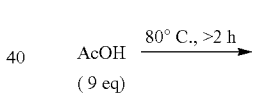

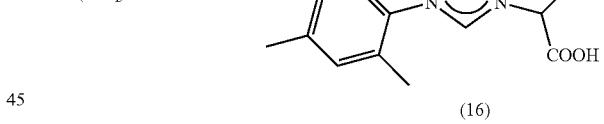
(16)

To determine the selectivity of the reaction, the reaction mixture comprising the 1-aryl-3-cycloalkyl-imidazolin-2-ylidene salt of formula 6 is cooled to room temperature. Then water is added, followed by solvent (for,example in ethyl acetate or dichloromethane). The aqueous phase is extracted (for example three times) with the solvent. The organic phases are combined and dried over an anionic salt (for example over magnesium sulphate). Then the organic phase is concentrated under vacuum, Nuclear magnetic resonance (NMR) analysis of the crude reaction product can allow the selectivity of the reaction to be determined.

Exchange of the acetate anion for another anion can be carried out as follows: the crude reaction product is dissolved in solvent (for example dichloromethane). Then 1 equivalent of the inorganic salt comprising the desired counter-anion is added (for example potassium tetrafluoroborate to obtain a tetrafluoroborate counter-anion). The mixture is then stirred at room temperature for some hours (for example 3 h). Then water is added and the organic phase is separated from the aqueous phase. The aqueous phase is washed (for example three times) with solvent. Each organic phase is dried over an anionic salt (for example over magnesium sulphate), and concentrated under vacuum. Generally a brown oil is obtained, to which a solvent is added (for example ethyl acetate). Then the mixture can be submitted to an ultrasound treatment for some minutes (for example 5 minutes). A solid forms, which is filtered on a frit, then washed with solvent (for example with ethyl acetate) to obtain the desired asymmetric imidazolium with a desired anion (for example a tetrafluoroborate anion).

Thus, following the general reaction scheme according to the invention, and using alpha-amino acids or beta-amino alcohols (namely heteroalkyls as compound of formula 3), which are preferably enantiomerically pure, and carrying out the counter-anion exchange as described above, the applicants were able to synthesize a large number of novel molecules. Notably, the applicants synthesized the asymmetric imidazolium salts of formulae 17 and 18:

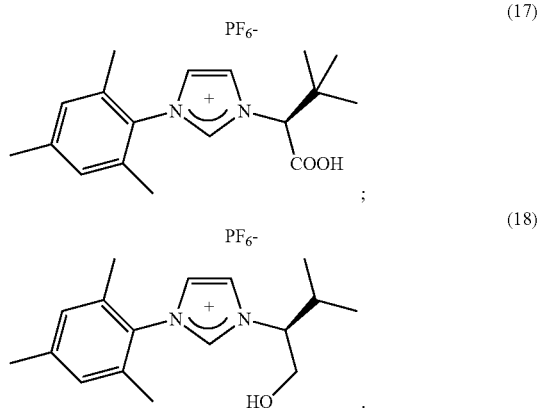

Moreover, when we wish to obtain salts in the form of zwitterions it is necessary to treat the intermediate asymmetric imidazolium salt, obtained according to the general reaction scheme described above, in a particular manner. It is necessary to provide dissolution of the intermediate asymmetric imidazolium salt in solvent (for example in ethyl acetate). The organic phase is then washed (for example twice) with a saturated solution of carbonate base (for example with a solution of sodium bicarbonate). The aqueous phases are combined and then evaporated, leading to a solid (generally of a yellow colour). The solid is then taken up in solvent (for example acetone), then filtered on a frit (notably to remove the inorganic salts). The filtrate is then evaporated. Zwitterionic asymmetric imidazolium salt is then formed. Regarding general formula 1A: A⁻ is a negative charge on group R2.

Following this procedure, the applicants were able to synthesize enantiomerically pure zwitterionic asymmetric imidazolium salts of formulae 19 and 20:

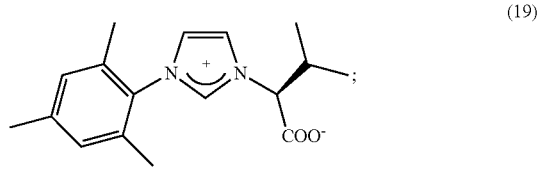

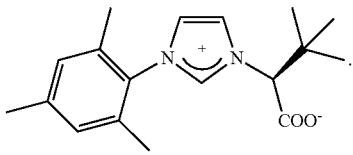

PRACTICAL EXAMPLES

1. Synthesis of a 1-Aryl-3-Cycloalkyl-Imidazolium-$BF_4^-$ Salt

Aniline (mesityl amine, 40 mmol, 1 eq) and the cycloalkyl amine (40 mmol, 1 eq) are put in a flask. Then acetic acid (10 mL, 18 mmol, 4.5 eq) is added slowly. The mixture is then stirred for 5 minutes.

Glyoxal (4.6 mL, 40 mmol, 1 eq), formal (3.0 ml, 40 mmol, 1 eq) and acetic acid (10 mL, 18 mmol, 4.5 eq) are put in a flask, then the mixture is heated to 80° C. The mixture of amines prepared previously is then added dropwise to this solution, then the mixture is left at 80° C. for the allotted time (from 2 h to 14 h).

Once the reaction has ended, the reaction mixture is cooled to room temperature and then water (20 mL) is added, followed by 40 mL of ethyl acetate (EtOAc). The aqueous phase is extracted three times with 20 mL of ethyl acetate (EtOAc), then the organic phases are combined and dried over magnesium sulphate ($MgSO_4$), and concentrated under vacuum. Nuclear magnetic resonance (NMR) analysis of the crude reaction product makes it possible to determine the selectivity of the reaction.

The crude reaction product is then dissolved in 70 mL of dichloromethane ($CH_2Cl_2$), and then 5.15 g of potassium tetrafluoroborate ($KBF_4$) (40 mmol, 1 eq) is added. The mixture is then stirred at room temperature for 3 h. Then liquid/liquid extraction is carried out, namely water/organic solvent extraction (here $H_2O/CH_2Cl_2$). For this, 20 mL of water is added, the phases are separated, and the aqueous phase is washed three times with 20 mL of dichloromethane ($CH_2Cl_2$). The organic phases are then combined, dried over magnesium sulphate ($MgSO_4$), and concentrated under vacuum. 40 mL of ethyl acetate (EtOAc) is then added to the resultant brown oil, and then the mixture is treated with ultrasound for 5 minutes. A solid forms, which is filtered on a frit, and then washed with ethyl acetate (EtOAc) to give the desired 1-aryl-3-cycloalkyl imidazolium.

Each desired 1-aryl-3-cycloalkyl imidazolium salt was submitted to NMR analysis and was confirmed by crystallographic analysis. Data from NMR analysis are given below for various 1-aryl-3-cycloalkyl imidazolium salts.

The $^1H$ (400 MHz), $^{13}C$ (125 MHz), $^{31}P$ (162 MHz), $^{11}B$ (128 MHz) and $^{19}F$ (376 MHz) NMR spectra were recorded on a Brucker ARX 400 Fourier transform spectrometer with proton decoupling for all the nuclei except $^1H$. The chemical shifts (δ) are expressed in parts per million (ppm), in the deuteratecl solvent indicated. The following abbreviations were used to denote the multiplicity of the signals: s (singlet), d (doublet), t (triplet), q (quadruplet), quin. (quintuplet), sept. (septuplet), m (multiplet), bs (broad singlet).

1a. 5-Cyclopentyl-2-Mesityl-Imidazolium Tetrafluoroborate

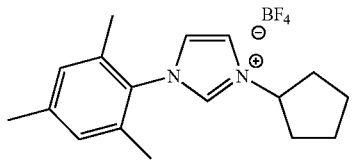

Empirical formula: $C_{17}H_{23}BF_4N_2$
M = 342.18 g/mol
Yield: 35%

Using the general procedure for preparing asymmetric imidazolium with 3.41 g (40 mmol) of cyclopentyl amine and 5.6 mL of mesityl amine (40 mmol) leads to 4.80 g (14 mmol, 35%) of asymmetric imidazolium in the form of a white solid.

Selectivity of the reaction:

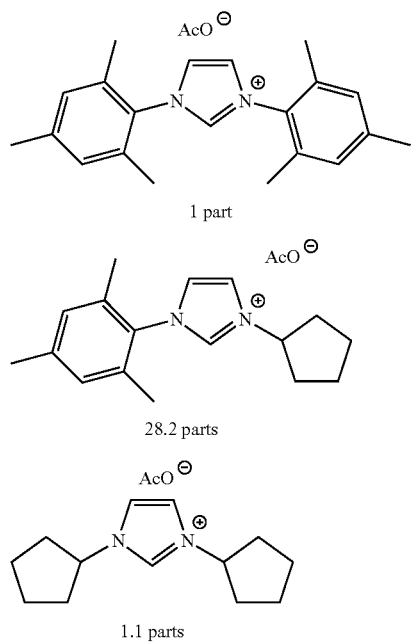

$^1$H (400 MHz, CDCl$_3$): 8.82 (t, J=1.73 Hz, 1H$_{im}$); 7.70 (t, J=1.7 Hz, 1H$_{im}$); 7.24 (t, J=1.7 Hz, 1H$_{im}$); 6.97 (s, 2H$_{ar}$); 5.03 (q, J=7.5 Hz, 1H); 2.42 (m, 2H); 2.32 (s, 3H$_{mes}$); 2.00 (s, 6H$_{mes}$); 1.92 (m, 4H); 1.77 (m, 2H)

$^{13}$C (125 MHz, CDCl$_3$): 141.31; 136,6; 134.4 (2C$_{mes}$); 130.8; 129.9 (2C$_{mes}$); 124.3 (C$_{im}$); 121.4(C$_{im}$); 62.0; 35.6 (2C); 24.0 (2C); 21.2; 17.3 (2C$_{mes}$)

$^{19}$F (376 MHz, CDCl$_3$): −151.98/−152.0 (s)

$^{11}$B (138 MHz, CDCl$_3$): −1.033 (s, BF$_4$)

Tm (melting point): 96° C.

HRMS (high-resolution mass spectrometry) [M$^+$]: Calculated: 255.18612 Found 255.1861.

1b. 5-Cyclohexyl-2-Mesityl-Imidazolium Tetrafluoroborate

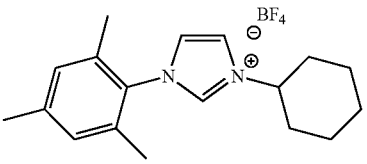

Empirical formula: $C_{18}H_{25}BF_4N_2$
M = 356.21 g/mol
Yield: 54%

Using the general procedure for preparing asymmetric imidazolium with 4.6 mL (40 mmol) of cyclohexylamine and 5.6 mL of mesityl amine (40 mmol) leads to 7.79 g (21.8 mmol, 54%) of asymmetric imidazolium in the form of a white solid.

Selectivity of the reaction:

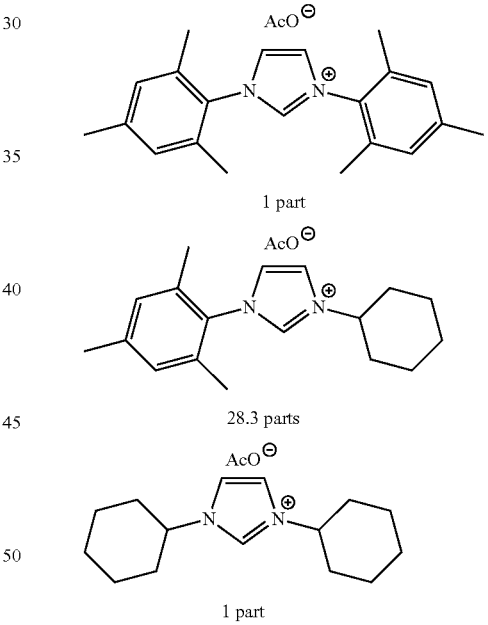

$^1$H (400 MHz, CDCl$_3$): 8.85 (t, J=1.8 Hz, 1H$_{im}$); 7.73 (t, J=1.8 Hz, 1H$_{im}$); 7.22 (t, J=1.8 Hz, 1H$_{im}$); 6.97 (s, 2H$_{ar}$); 4.58 (m, 1H); 2.32 (s, 3H$_{mes}$); 2.21 (m, 2H); 2.00 (s, 6H$_{mes}$); 1.89 (m, 2H); 1.75 (m, 3H); 1.51 (m, 2H); 1.29 (m, 1H)

$^{13}$C (125 MHz, CDCl$_3$): 141.3; 135.7; 134.4 (2C$_{mes}$); 130.9; 129.9 (2C$_{mes}$); 123.9 (C$_{im}$); 121.1(C$_{im}$); 60.5; 33.6 (2C); 25.0 (2C); 24.7; 21.2; 17.3 (2C$_{mes}$)

$^{19}$F (376 MHz, CDCl$_3$): −151.74 (s)

$^{11}$B (138 MHz, CDCl$_3$): −0.992 (s, BF$_4$)

Tm: 170° C.

HRMS [M$^+$]: Calculated: 269.20177 Found 269.2019.

1c. 5-Cycloheptyl-2-Mesityl-Imidazolium Tetrafluoroborate

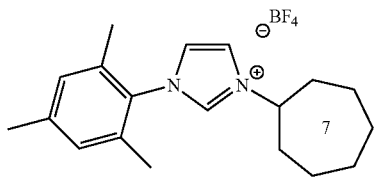

Empirical formula: $C_{19}H_{27}BF_4N_2$
M = 370.24 g/mol
Yield: 68%

Using the general procedure for preparing asymmetric imidazolium with 2.55 mL (20 mmol) of cycloheptylamine and 2.8 mL of mesityl amine (20 mmol) leads to 5.03 g (13.6 mmol, 68%) of asymmetric imidazolium in the form of a white solid.

Selectivity of the reaction:

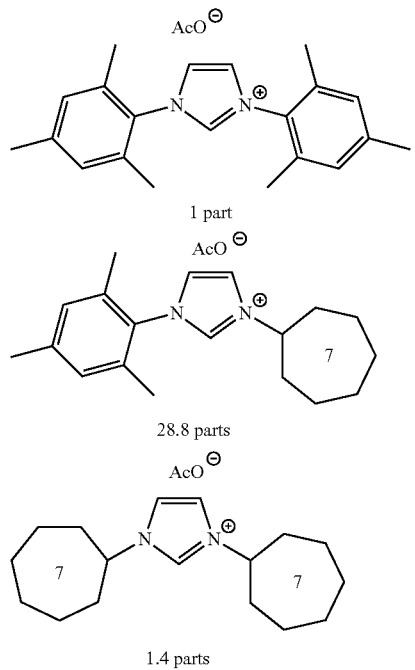

$^1$H (400 MHz, CDCl$_3$): 8.85 (t, J=1.8 Hz, 1H$_{im}$); 7.72 (t, J=1.8 Hz, 1H$_{im}$); 7.22 (t, J=1.8 Hz, 1H$_{im}$); 6.97 (s, 2H$_{ar}$); 4.76 (m, 1H); 2.31 (s, 3H$_{mes}$); 2.21 (m, 2H); 1.99 (m, 2H+6H$_{mes}$); 1.80 (m, 2H); 1.62 (m, 6H)

$^{13}$C (125 MHz, CDCl$_3$): 141.2; 135.5; 134.4 (2C$_{mes}$); 130.9; 129.8 (2C$_{mes}$); 124.1 (C$_{im}$); 121.1(C$_{im}$); 62.8; 36.0 (2C); 27.0 (2C); 24.1 (2C); 21.2; 17.3 (2C$_{mes}$)

$^{19}$F (376 MHz, CDCl$_3$): −151.6 (s)

$^{11}$B (138 MHz, CDCl$_3$): −0.979 (s, BF$_4$)

Tm: 185° C.

HRMS [M$^+$]: Calculated: 283.21742 Found: 283.2173.

1d. 5-Cyclooctyl-2-Mesityl-Imidazolium Tetrafluoroborate

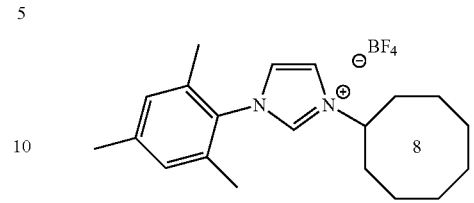

Empirical formula: $C_{20}H_{29}BF_4N_2$
M = 384.26 g/mol
Yield: 43%

Using the general procedure for preparing asymmetric imidazolium with 5.6 mL (40 mmol) of cyclooctylamine and 5.6 mL of mesityl amine (40 mmol) leads to 6.61 g (17.2 mmol, 43%) of asymmetric imidazolium in the form of a white solid.

Selectivity of the reaction:

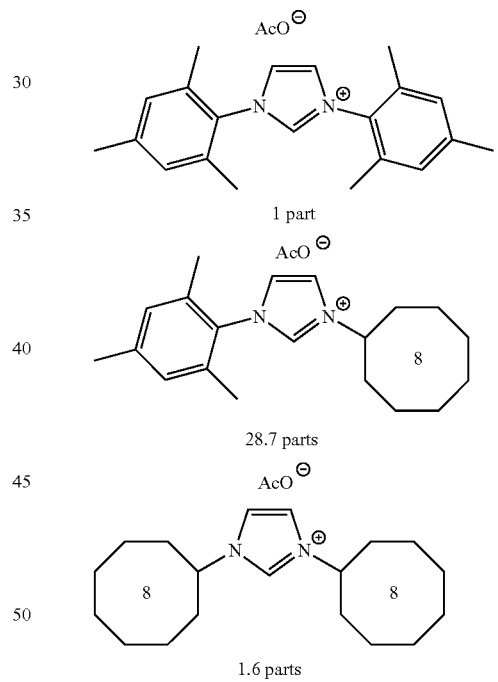

$^1$H (400 MHz, CDCl$_3$): 8.86 (t, J=1.7 Hz, 1H$_{im}$); 7.70 (t, J=1.7 Hz, 1H$_{im}$); 7.23 (t, J=1.7 Hz, 1H$_{im}$); 6.97 (s, 2H,), 4.58 (q, J=6.8 Hz, 1H); 2.31 (s, 3H$_{mes}$); 2.11 (m, 4H); 2.00 (s, 6H$_{mes}$); 1.63 (m, 10H)

$^{13}$C (125 MHz, CDCl$_3$): 141.2; 135.5; 134.4 (2C$_{mes}$); 130.9; 129.9 (2C$_{mes}$); 124.1 (C$_{im}$); 121.3(C$_{im}$); 62.1; 33.9 (2C); 26.3 (2C); 25.5; 23,9; 21.2; 17.3 (2C$_{mes}$)

$^{19}$F (376 MHz, CDCl$_3$): −151.6 (s)

$^{11}$B (138 MHz, CDCl$_3$): −0.990 (s, BF$_4$)

Tm: 175° C.

HRMS [M$^+$]: Calculated: 297,23307 Found: 297.2332.

1e. 5-Cyclododecyl-2-Mesityl-Imidazolium Tetrafluoroborate

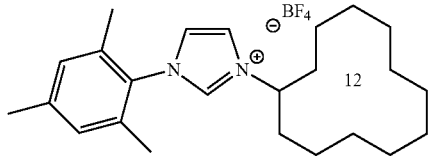

Empirical formula: $C_{24}H_{37}BF_4N_2$
M = 440.37 g/mol
Yield: 62%

Using the general procedure for preparing asymmetric imidazolium with 7.6 mL (40 mmol) of cyclododecylamine and 5.6 mL of mesityl amine (40 mmol) leads to 10.90 g (24.8 mmol, 62%) of asymmetric imidazolium in the form of a white solid.

Selectivity of the reaction:

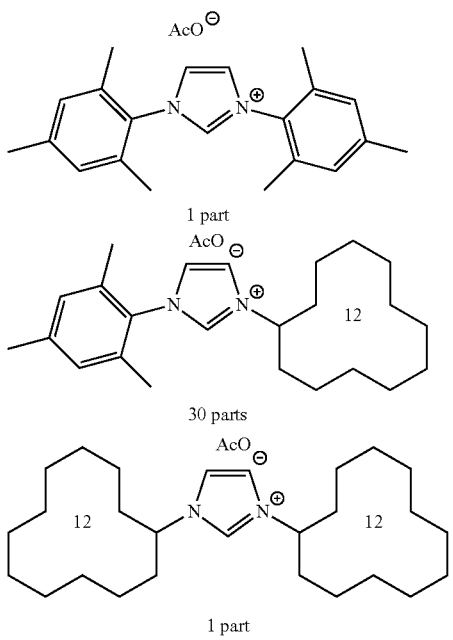

1 part 30 parts 1 part $^1$H (400 MHz, CDCl$_3$): 8.86 (t, J=1.8 Hz, 1H$_{im}$); 7.73 (t, J=1.8 Hz, 1H$_{im}$); 7.27 (t, J=1.8 Hz, 1H$_{im}$); 6.96 (s, 2H$_{ar}$); 4.74 (m, 1H); 2.31 (s, 3H$_{mes}$); 2.11 (m, 2H); 2.00 (s, 6H$_{mes}$); 1.83 (m, 2H); 1.40 (m, 18H)

$^{13}$C (125 MHz, CDCl$_3$): 141.1; 135.9; 134.4 (2C$_{mes}$); 130.9; 129.8 (2C$_{mes}$); 124.2 (C$_{im}$); 121.9(C$_{im}$); 59.4; 30.2 (2C); 23.7; 23.4 (2C); 23.35(2C); 23.3(2C); 21.4(2C); 21.2; 17.2 (2C$_{mes}$)

$^{19}$F (376 MHz, CDCl$_3$): −151.4/−151.6 (s)

$^{11}$B (138 MHz, CDCl$_3$): −1,033 (s, BF$_4$)

Tm: 177° C.

HRMS [M$^+$]: Calculated: 353.29567 Found 353.2956.

1f. 5-Cyclododecyl-2-(3,5-Dimethylphenyl)-Imidazolium Tetrafluoroborate

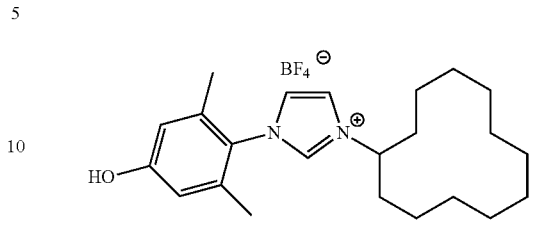

Empirical formula: $C_{23}H_{35}BF_4N_2O$
M = 442.34 g/mol
Yield: 70%

Using the general procedure for preparing asymmetric imidazolium with 1.37 g (10 mmol; 1 eq.) of 4-amino-3,5-dimethylphenol and 1.83 g (10 mmol, 1 eq.) of cyclododecylamine leads to 3.10 g (7 mmol, 70%) of the expected product in the form of a brown solid.

Selectivity of the reaction:

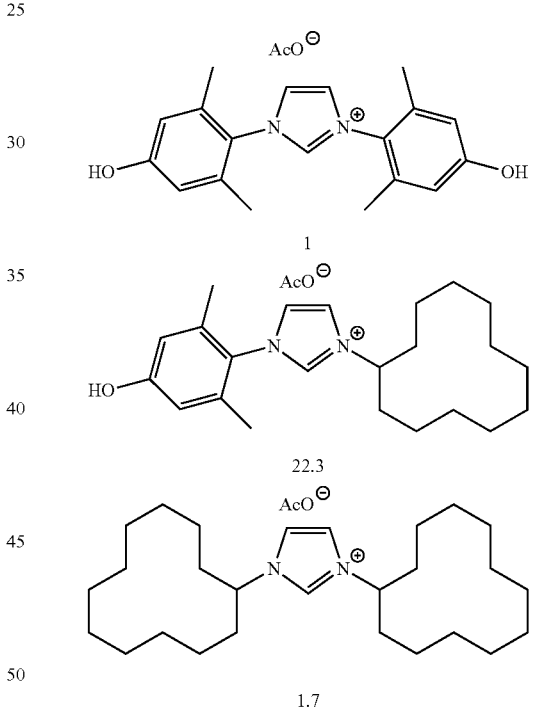

1

22.3

1.7

$^1$H (400 Mz, CD$_3$OD): 9.39 (s, 1H), 8.06 (d, $^3J_{H-H}$=1.98 Hz, 1H), 7.72 (d, $^3J_{H-H}$=1.9 Hz, 1H), 6.70 (s, 2H), 4.72 (m, 1H), 2.27-2.16 (m, 2H), 2.03 (s, 6H), 1.94-1.84 (m, 2H), 1.63-1.32 (m, 18H)

$^{19}$F (128 MHz, CDCl$_3$): −154.4 (s)

$^{11}$B (400 MHz, CD$_3$OD): −1.2 (s)

2. Synthesis of the (S)-2-(Mesitylimidazolium)-3-Methyl Butanoate Zwitterionic Salt Using the general procedure for obtaining asymmetric imidazolium salts with 1.17 g of (L)-valine (10 mmol, 1 equiv.), 1.4 mL (10 mmol, 1 equiv.) of mesityl amine makes it possible to obtain the acetate salt.

1.17 g of (L)-valine (10 mmol, 1 eq) and 1.4 mL (10 mmol, 1 eq) of mesityl amine are put in a flask. Then acetic acid (10 mL, 18 mmol, 4.5 eq) is added slowly. The mixture is then stirred for 5 minutes.

Glyoxal (4.6 mL, 40 mmol, 1 eq), formol (3.0 mL, 40 mmol, 1 eq) and acetic acid (10 mL, 18 mmol, 4.5 eq) are put in a flask, then the mixture is heated to 80° C. The valine/mesityl amine mixture prepared previously is then added dropwise to this solution, and then the mixture is left at 80° C. for the allotted time (from 2 h to 14 h).

Once the reaction has ended, the reaction mixture is cooled to room temperature and then water (20 mL) is added, followed by 40 mL of ethyl acetate (EtOAc).

After dissolving the crude reaction product in ethyl acetate (EtOAc) (10 mL), the organic phase is washed twice with 5 mL of a saturated solution of sodium bicarbonate (NaHCO$_3$), then the aqueous phases are combined and then evaporated, leading to a yellow solid. The solid is then taken up in acetone, then filtered on a frit (to remove the inorganic salts). The filtrate is then evaporated to give 1.00 g (3.5 mmol, 35%) of (S)-2-(mesitylimidazolium)-3-methyl butanoate in the form of a yellowish solid.

The (S)-2-(mesitylimidazolium)-3-methyl butanoate zwitterionic salt was submitted to NMR analysis and was confirmed by crystallographic analysis. Data from NMR analysis are presented below (the abbreviations and conditions being similar to what is described above):

$^1$H (400 MHz, CDCl$_3$): 9.28 (s, 1H); 7.84 (bs, 1H); 7.08 (bs, 1H); 6.83 (bs, 2H); 4.66 (d, J=7.5 Hz, 1H); 2.34 (hex., J=6.7 Hz, 1H); 2.17 (bs, 3H); 1.87 (bs, 6H); 0.85 (d, J=6.7 Hz, 3H); 0.69 (d, J=6.7 Hz, 3H).

$^{13}$C (125 MHz, CDCl$_3$): 174.6; 170.4; 141.5; 137.1; 131.0; 130.0; 124.3; 121.5; 73.0; 32.6; 21.7; 21.2; 19.9; 18.6.

HRMS [M+]: Calculated: 287.17595 Found 287.1757.

3. Synthesis of the (S)-2-(Mesitylimidazolium)-3,3-Dimethyl Butanoate Zwitterionic Salt Using the general procedure for obtaining asymmetric imidazolium salts with 0.262 g (0.2 mmol, 1 eq) of ter-leucine, 0.28 mL (0.2 mmol, 1 eq) of mesityl amine makes it possible to obtain the acetate salt.

0.262 g (0.2 mmol, 1 eq) of ter-leucine and 0.28 mL (0.2 mmol, 1 eq) of mesityl amine are put in a flask. Then acetic acid (10 mL, 18 mmol, 4.5 eq) is added slowly. The mixture is then stirred for 5 minutes.

Glyoxal (4.6 mL, 40 mmol, 1 eq), formol (3.0 mL, 40 mmol, 1 eq) and acetic acid (10 mL, 18 mmol, 4.5 eq) are put in a flask, and then the mixture is heated to 80° C. The valine/mesityl amine mixture prepared previously is then added dropwise to this solution, and then the mixture is left at 80° C. for the allotted time (from 2 h to 14 h).

Once the reaction has ended, the reaction mixture is cooled to room temperature and then water (20 mL) is added, followed by 40 mL of ethyl acetate (EtOAc), After dissolving the crude reaction product in EtOAc (3 mL), the organic phase is washed twice with a saturated solution of NaHCO$_3$ and then the aqueous phases are combined and then evaporated, leading to a yellow solid. The solid is taken up in acetone, and then filtered on a frit. The filtrate is then evaporated to give 0.106 g (0.035 mmol, 17%) of (S)-2-(mesitylimiclazolium)-3,3-dimethyl butanoate in the form of a white solid.

The (S)-2-(mesitylimidazolium)-3,3-dimethyl butanoate zwitterionic salt was submitted to NMR analysis and was confirmed by crystallographic analysis. Data from NMR analysis are presented below (the abbreviations and conditions being similar to what is described above):

$^1$H (400 MHz, CDCl$_3$): 9.17 (s, 1H); 7.87 (s, 1H); 7.11 (s, 1H); 7.00 (s, 2H); 4.80 (s, 1H); 2.34 (s, 3H); 2.24 (bs; 2H); 2.00 (s, 6H); 1.00 (s, 9H).

$^{19}$F (376 MHz, CDCl$_3$): −71.43; −73.32

$^{31}$P (162 MHz, CDCl$_3$): −135.6; −140.0; −144.4; −148.8; −153.2

HRMS [M$^+$]: Calculated: 301.19160 Found: 301.1913.

An advantage of the present invention, namely synthesis of asymmetric imidazolium salts having groups R1 and R2 as described above, is that it confers good stability (probably because of the considerable steric interactions). As the imidazolin-2-ylidene carbene is stable, this avoids the parasitic reaction of dimerization of the carbene species with itself as described in NHCs in Synthesis, S. P. Nolan, Ed., 2006, Wiley-VCH. Accordingly, good yields for synthesis of target organometallic complexes are observed. The present invention offers an unpublished route for synthesizing precursor salts of diaminocarbenes of the 1-aryl-3-cycloalkyl-imidazolin-2-ylidene or 1-aryl-3-heteroalkyl-imidazolin-2-ylidene type.

This unpublished production route is rapid, efficient (just one chemical operation) making it possible to generate 1,3-disubstituted asymmetric imidazolium salts bearing an aromatic group on the one hand, and a cycloalkyl (or heteroalkyl) group on the other hand.

The invention claimed is:

1. Method of preparing an intermediate asymmetric imidazolium salt of formula 1A:

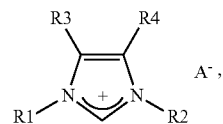

(1A)

in which

R1 is an aromatic group,

R2 is selected from a secondary cyclic aliphatic alkyl group and a heteroalkyl group, R3 and R4 are selected independently of one another from the group consisting of hydrogen, a halide and an alkyl group, and A− is an anion, comprising the following steps:

a. forming a reaction mixture by contacting one equivalent (1 eq) of an aniline of formula 2:

(2)

with one equivalent (1 eq) of a compound of formula 3:

(3)

in the presence of at least four point five equivalents (4.5 eq) of a Brønsted acid of formula 4:

AH  (4);

b. forming a solution comprising one equivalent (1 eq) of a dicarbonyl of formula 5

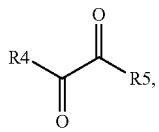
(5)

one equivalent (1 eq) of formaldehyde, and at least four point five equivalents (4.5 eq) of the Brønsted acid of formula 4, heating said solution to about 80° C. and then adding the reaction mixture formed in step a.;
c. stirring for at least 2 hours at about 80° C.; and
d. isolating the intermediate asymmetric imidazolium salt of formula 1A.

2. Method of preparing an asymmetric imidazolium salt of formula 1B:

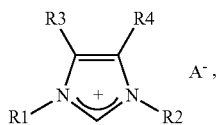
(1B)

in which
R1 is an aromatic group,
R2 is selected from a secondary cyclic aliphatic alkyl group and a heteroalkyl group,
R3 and R4 are selected independently of one another from the group consisting of hydrogen, a halide and an alkyl group, and
A− is selected from the group consisting of a tetrafluoroborate anion, a hexafluorophosphate anion, a hexafluoroantimony anion, a tetrakis[(3,5-trifluoromethyl)phenyl]borate anion and a halide anion,
said method comprising steps a. to d. according to claim 1, and further comprising the steps of:
e. adding one equivalent (1 eq) of an inorganic salt and solvent, preferably dichloromethane, to the intermediate asymmetric imidazolium salt isolated in step d.;
f. stirring at room temperature for at least one hour and carrying out water/organic solvent extraction followed by evaporation of said organic solvent;
g. precipitating by a polar organic solvent, then isolating the asymmetric imidazolium salt of formula 1B.

3. Method of preparing an asymmetric imidazolium salt according to claim 2, in which the inorganic salt in step e. is selected from the group consisting of potassium tetrafluoroborate, sodium tetrafluoroborate, lithium tetrafluoroborate, hydrogen tetrafluoroborate, ammonium tetrafluoroborate, potassium hexafluorophosphate, sodium hexafluorophosphate, lithium hexafluorophosphate, hydrogen hexafluorophosphate, ammonium hexafluorophosphate, silver hexafluoroantimony, potassium hexafluoroantimony, sodium hexafluoroantimony, lithium hexafluoroantimony, potassium tetrakis[(3,5-trifluoromethyl)phenyl]borate, sodium tetrakis[(3,5-trifluoromethyl)phenyl]borate and lithium tetrakis[(3,5-trifluoromethyl)phenyl]borate and halogen acid.

4. Method of preparing an asymmetric imidazolium salt of formula 1C:

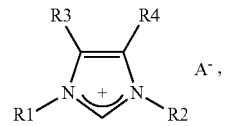
(1C)

in which
R1 is an aromatic group,
R2 is a heteroalkyl group,
R3 and R4 are selected independently of one another from the group consisting of hydrogen, a halide and an alkyl group, and
A− is a negative charge on group R2,
said method comprising steps a. to d. according to claim 1, and further comprising the steps of:
h. adding at least ten equivalents (10 eq) of a carbonate base to the intermediate asymmetric imidazolium salt isolated in step d.;
i. isolating the asymmetric imidazolium salt of formula 1C.

5. Method of preparing an asymmetric imidazolium salt according to claim 4, in which said carbonate base in step h. is selected from the group consisting of sodium bicarbonate, potassium bicarbonate, sodium hydrogen carbonate and potassium hydrogen carbonate.

6. Method according to claim, in which the Brønsted acid of formula 4 in said steps a. and b. is acetic acid.

7. Method according to claim 1, in which R1 is selected from the group consisting of 2,4,6-trimethylphenyl, 3,5-dinitrophenyl, 2,4,6-tris(trifluoromethyl)phenyl, 2,4,6-trichlorophenyl, and hexafluorophenyl.

8. Method according to one of claim 1, in which R2 is selected from the group consisting of cyclopentyl, cyclohexyl, cyclooctyl, cyclodecyl, cyclododecyl, and cyclopentadecyl.

9. Method according to claim 4, in which R2 is selected from the group consisting of 3-methyl butanoate and 3,3-dimethyl butanoate.

10. Method according to claim 1, in which R3 and R4 are each hydrogen.

11. Asymmetric imidazolium salt of formula 1D comprising:

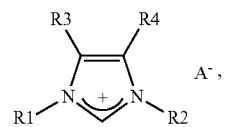
(1D)

in which
R1 is selected from the group consisting of 2,4,6-trimethlphenyl, 3,5-dinitrophenyl, 2,4,6-tris(trifluoromethyl) phenyl, 2,4,6-trichlorophenyl, and hexafluorophenyl,
R2 is a secondary cyclic aliphatic alkyl group,
R3 and R4 are selected independently of one another from the group consisting of hydrogen, a halide and an alkyl group, and
A− is an anion selected from the group consisting of a tetrafluoroborate anion, a hexafluorophosphate anion, an acetate anion, a hexafluoroantimony anion, a tetrakis[(3,5-trifluoromethyl)phenyl]borate anion and a halide anion.

12. Asymmetric imidazolium salt according to claim 11, in which R2 is selected from the group consisting of cyclopentyl, cyclohexyl, cycloheptyl, cyclooctyl, cyclodecyl, cyclododecyl, and cyclopentadecyl.

13. Asymmetric imidazolium salt according to claim 11, in which R3 and R4 are each hydrogen.

\* \* \* \* \*